United States Patent [19]

Takács et al.

[11] 4,315,923

[45] Feb. 16, 1982

[54] PROCESS FOR THE PRODUCTION OF ORGAN EXTRACTS WITH HIGH HERPARIN CONTENT

[75] Inventors: Istvan Takács; György Kerey; János Illés; Péter Rudolf; Pál Gere; László Czebe; Erzsébet Neszmélyi, all of Budapest, Hungary

[73] Assignee: Richter Gedeon Vegyészeti Gyár RT, Budapest, Hungary

[21] Appl. No.: 131,824

[22] Filed: Mar. 19, 1980

[30] Foreign Application Priority Data

Mar. 21, 1979 [HU] Hungary ............................. RI 705

[51] Int. Cl.³ ..................... A61K 31/725; C08B 37/10
[52] U.S. Cl. ..................................... 424/183; 536/21
[58] Field of Search ......................... 536/21; 424/183

[56] References Cited

U.S. PATENT DOCUMENTS 2,571,679 10/1951 Butturini et al. ..................... 536/21
2,989,438 6/1961 Nomine et al. ..................... 424/183
3,865,723 2/1975 Marchisio et al. .................. 424/183
4,175,182 11/1979 Schmer .............................. 424/183

FOREIGN PATENT DOCUMENTS 950594 10/1956 Fed. Rep. of Germany ...... 424/183
872214 7/1961 United Kingdom ................. 536/21
1221784 2/1971 United Kingdom ................. 536/21

Primary Examiner—Johnnie R. Brown
Attorney, Agent, or Firm—Karl F. Ross

[57] ABSTRACT

A process for producing an aqueous solution of high heparin content from heparin-containing animal organs comprises forming a heparin-enriched granular raw material from these organs and extracting the raw material at a temperature of 20° to 80° C. with a salt solution having a salt concentration of 1.5 to 12.0% and a pH in the range of 8 to 12.8 or an alkalinity of 0.5 normal to 1.08 normal concentration. The dry substance to liquid ratio should be 1:5.

4 Claims, No Drawings

PROCESS FOR THE PRODUCTION OF ORGAN EXTRACTS WITH HIGH HERPARIN CONTENT

FIELD OF THE INVENTION

The invention relates to a process for the production of organ extracts with heparin content from heparin-containing raw materials via counterflow extraction in watery medium.

It is generally known that processing of the heparin-containing animal organs, extraction of the heparin are costly and complicated and can be realized as a result of an extraction process consisting of several consecutive steps for different purposes.

The organ extraction process actually can not be separated from the collection and preservation method of the heparin-containing animal organs, since these processes decisively influence the industrial implementation of the extraction process and also the magnitude of the attainable yields.

The heparin extraction processes require long processing time and their reproducibility is doubtful; consequently both the technical and patent literature are intensively concerned with extraction processes and the effectiveness and economic efficiency of complete heparin production methods.

It is obvious that the most important objective of the extraction is the most effective dissolution of the active ingredient content of the various types of raw materials to be processed after organ collection and storage with the aid of procedures which do not cause any deterioration or decomposition of the existing active ingredient content.

A further objective is the isolation of an end product of pharmaceutical quality from the aqueous heparin-containing solutions obtained by the extraction process and accomplished with satisfactory yield and in a few steps.

For this purpose it is necessary that the heparin extract liquid should contain the least possible amount of pollutants such as heparinoid pyrogen coloring polypeptide substances which interfere with the purification. The most selective dissolution of the heparin is expedient taking into account that other components present in the organ extract (fats, lipoids, proteins, peptides, inorganic salts) inhibit the isolation of heparin, i.e. reduce the attainable yield, causing problems frustrating operative implementation. Furthermore, the end product will not be always completely purifiable from all the accompanying materials.

The foregoing objectives have not been successfully realized optimally and jointly in earlier processes.

The three fundamental methods hitherto used in the extraction of the heparin-containing animal organs are outlined below:

Charles and Scott, J. Biol, Chem. 102, 425, 1933, have proposed the use of the intrinsic hydrolyzing enzymes of the surviving tissues for the extraction of the heparin-containing, cut-up, deep frozen organ. Autolysis is carried out for a long period and then, in order to coagulate the extract, a mildly alkaline salt solution and boiling are used. The methods operating with autolysis are described in the U.S. Pat. Nos. 2,571,697 and 2,797,184. The autolysis can be combined with further extraction improving processes as described in the U.S. Pat. Nos. 2,884,358 and 3,016,331.

Disadvantages of the extraction method using autolysis are described in Hungarian patent No. 148 776 and U.S. Pat. No. 2,587,924. The disadvantage based on experimental data can be attributed to several reasons:

Assuming a state of equilibrium between the extracting solution and the organ to be extracted in the process of extraction, the high moisture content of the extracted organ is associated with considerable loss of heparin has to be reckoned with. Removal of the extracted organ necessarily involves the removal of moisture (and heparin solution) from the system. Due to the different degree of autolysis of the medium, the state of balance does not set in on every occasion the equilibrium state liquid, is not always reached and the loss is naturally higher.

During the organ storage process prior to autolysis and during autolysis heparin-damaging microorganisms propagate, as a result of which the yield diminishes. The bacterial contamination is disadvantageous in other respects as well (pyrogenicity, toxicity).

One of the main problems of the methods operating with autolysis is attributed to organ collection which causes uncertain compositions of the obtained extract. Due to the developed large volume, the equipment demand necessary for this phase of the process is also significant. Implementation of the process from industrial point of view is possible only if the volume is reduced to such extent that it should yield heparin-containing product of at least 1–10% purity. Due to the composition fluctuations, the quality of the obtained product varies and economical production is difficult to realize.

In a second extraction method the active ingredient content of the heparin-containing organs is recovered by the use of chemicals, with dissolution of the heparin or heparin-protein complex. These processes are described for instance in the Hungarian patents No. 948 776 and No. 149 339, English patent specification No. 992 201, U.S. Pat. Nos. 2,623,001, 3,058,884 and 3,262,854.

However, the solvent extraction has the drawback that as in the autolysis method, organ residues of high moisture content have to be removed from the system, whereby a significant loss of heparin amounting to 20–40% has to be reckoned with depending on the organic dry substance concentration of the extraction residue (compare the example given in the Hungarian patent No. 148 776 and English patent specification No. 992 201).

The composition variation of the utilized organs is also unfavorable also in this method.

Owing to these difficulties the method of U.S. pat. No. 2,623,001 describes a lengthy dialysis in large volume following the recovery. The method described in the U.S. Pat. No. 3,262,854 uses organic solvent as a matter of necessity in the phases of the largest volume of the extraction.

Summarizing the methods of the first group using autolysis and those of the second group operating with chemical extraction only, it appears to be a common disadvantage that during the extraction (usually a uniflow process carried out only in one or two steps due to the consistency of the raw materials generally used until recently) the obtained solutions contain several accompanying and disturbing impurities and their heparin concentration is very low being 10–20 NE/ml, or 0.01% in average. In other words for the recovery of 1000 MNE (6.5 kg) heparin, the extraction is carried out with a volume of 50 000-100 000 liters and a minimum 20% loss of heparin.

The third group of the extraction methods - in order to reduce the loss of heparin and to eliminate the uncertainty of autolysis - submits the heparin-containing organs without chemicals to an intensive and lengthy proteolysis extending to substantially complete dissolution with the use of an enzyme, as trypsin, pancreas-extract, papain, fed from the outside into the system.

Such processes are described for instance in the Hungarian patent No. 147 323, the U.S. Pat. Nos. 2,587,924, 2,989,438 and 3,817,924, as well as in the U.S. pat. No. 2,884,358 and 3,016,331, using combined autolysis and enzyme proteolysis. Despite the existing advantageous effects the economic efficiency of the latter extraction process is sensitive to the cost of the proteolytic enzyme necessary for the specific amount of the organ. For instance the admission of 1.5–3 kg pancreas or pancreas residue is necessary for 2 kg heparin-containing organ in one of the mentioned processes.

If the specific quantity of the enzymes is reduced, the proteolysis and filtration process become extremely prolonged. In the U.S. Pat. No. 3,817,831 the pepsin autolysis lasts for 24 hours, the autolysis carried out with pancreatin for 15 hours, after which first coarse, then after a lapse of 24 hours ultrafiltration is used. The extended-time processes increase the risk of bacterial contamination, while the presence of the enzymes in materials supplied from the outside breaks down the glucoside bonds of heparin or otherwise increase the heparin decomposition.

As a result of the complete or nearly complete proteolysis the components present in the animal organs and accompanying the heparin are dissolved, such as the muco-polysaccharide type compounds, nuclein acid-derivatives, fats, lipoids, which considerably complicate fast and efficient further processing. According to example 3 in the U.S. Pat. No. 3,817,831 after completion of the proteolysis and coarse filtering the proportion of organic dry substance content is 10–35%, i.e. three times higher for the 0.027% heparin content in solution B. For this reason the discharge of processed solutions free from active ingredient is problematic in respect to environmental protection. The product of the processes operating with proteolysis is an extremely dilute solution of 6.45 NE/ml (0.004–0.03%) concentration; in a more concentrated solution the proteolysis can not be carried out, due to substratum-inhibition.

Extraction of animal organs, i.e. dissolution of the heparin content present in them, and reduction of the volume of the solutions efficiently and reproducibly is the lengthiest and most complicated phase of the complete production process for the production of this pharmaceutical product. The extraction takes a long time, due to the proteolysis and/or series of chemical-physical processes carries out in several steps, because the extremely low active ingredient concentration necessitates the installation and operation of equipment of very large volume.

The economic efficiency of chemical extraction is adversely influenced by the chemicals to be used, and by cost of the enzymes at the proteolytic extraction. The reproducibility is uncertain, because due to different collection and storage methods for the animal organs, the active ingredient content fluctuates between wide limits. The further processing is also aggravated by the impurities present in a several times greater quantity.

Thus the conventional organ collection methods used in the heparin production do not make it possible to obtain an end product of pharmacological quality without loss or only with a small loss of the heparin content found in the course of the usual and large volume storage of the organs.

OBJECTS OF THE INVENTION

The invention has as its objects simplification of the extraction and reduction of the time of this production phase, increasing the economic efficiency, improving the selectivity whereby extracts of extremely high, at least 120 NE/ml concentration, constant composition, containing minimal disturbing impurities are produced with less energy and other costs.

DESCRIPTION OF THE INVENTION

The process according to the invention for the production of aqueous extracts of constant composition with extremely high, at least 120 NE/ml heparin content comprises subjecting a heparin-enriched, amorphous granular, retentive raw material with 90–95% dry substance content and large specific surface to intermittent or continuous counterflow extraction in aqueous medium in optimal temperature range and at pH value specified for the given processing system and raw material with the use of a salt solution.

The counterflow extraction is carried out at temperature between 20° to 80° C. in 1.5–12.0% electrolyte (salt) concentration and in 8–12.8 pH range or in an alkaline solution of 0.5–1.0 concentration.

The electrolyte concentration, the temperature and pH values are kept at constant value during the counterflow extraction process. The proportion of the extracting salt solution is set with respect to the dry organ in such a way that extract liquids of 150–300 NE/ml concentration should be obtained. For this purpose it is necessary to have the dry substance—liquid ratio be 1:5 during the whole process. The used base of a valence of one or more is usually sodium hydroxide or another alkaline solution normal in the heparin extraction, while the electrolyte is a cation of one or more valence and is a cation inert with respect to the heparin, of a salt with organic or inorganic anions, preferably sodium chloride. The heparin-enriched raw material is a material the heparin content of which is higher by 5–35% compared to any natural raw material, calculated with respect to the dry substance content of the organ.

The counterflow extraction is carried out in a single piece of equipment intermittently with evacuation methods or continuously, suitably in a vibrating U-extractor. The U-extractor is described in the Hungarian patent specification No. 159 977 and is particularly effectively used according to the invention for the production of aqueous extracts with high heparin content. In this equipment the granular, heparin-containing raw material to be extracted is treated by (a) preliminary uniflow spraying, (b) uniflow spraying, (c) uniflow liquid preliminary extraction, (d) counterflow soaking vibrated extraction, and (e) liquid afterextraction, in succession.

The equipment is built up on the cell system, the possibility of back mixing of the watery extracts between the cells is inhibited and at the same time, the vibrated units of the equipment considerably facilitate the setting of the extraction balance pertinent to the given point of time. Its advantage is that both the proportion of the extraction liquid calculated to the material to be extracted and the time of extraction as well as the length of the extraction path can be significantly reduced.

In the process according to the invention, heparin-concentrated, dried, amorphous granular, organ concentrate a large specific surface was used as produced by the process described in the Hungarian patent application No. RI-705 and summarized below.

The heparin-containing raw materials of enriched active ingredient content, constant composition, low fat content and germ number, storable without change in the morphology and active ingredient content, starting out from animal organs, is prepared by storing the heparin-containing animal organs—if necessary after cutting up—in a wet medium in 10° to 50° C. temperature range for 0.15 to 15 hours. The heparin-containing complex insoluble in water is separated from the pretreated suspension at a temperature between 75° and 100° C., this complex being transformed to easily filterable aggregates by further heat treatment. The flocculated precipitation is separated and the isolated heparin-containing raw material is dried at 100° C. temperature until 90—95% dry substance content is reached and a friable product is obtained.

The initial raw material is preferably pig's small intestine, mucosa, seroza, cattle lung, but all other heparin-containing organs, such as small intestine of cattle, sheep, cattle spleen, other entrails and liver may be used for this purpose.

When mucosa is used, the cutting and aqueous dilution are not necessary.

The other animal organs are cut up to 4-6 mm size and an aqueous suspension is prepared, which includes the heparin and proteins to various degree in solution and also in the form of colloidal solution.

The aqueous suspension is set to 1.5 0 17% dry substance content. The dilution is carried out with water preferably of 36°-42° C. temperature. Thus the external heating at the pretreatment is not necessary or heating is required only to a low degree.

Starting with the usual heparin-containing materials, the suspension obtained is pretreated in a temperature range of 30° to 50° C. generally for 2 to 6 hours.

After pretreatment, precipitation of the heparin-protein complex is carried out by direct steam blowing or by heat treatment for a longer period, while the main part of the heparin is fixed to the filterable proteins.

The heat treatment is carried out continuously at or over 85° C. for a minimum of 2 minutes and for 15 minutes, or longer in an intermittent system.

By precipitation of the proteins favorable grain size is obtained with respect to the filtration-isolation, and the virulent germs are destroyed at the same time. The precipitate is isolated with about 20-25% dry substance content in a mechanical separator functioning by gravity.

The mechanical separator should have a continuously regenerating filter surface, but continuous or intermittent flat sieves, curved sieves, centrifuges and worm separators are also applicable.

The discharged filtrate may contain 5-25% of the original dry substance content, and depending on the controlled pretreatment it is composed of nonheat-denaturable proteins, peptides, nucleic acid derivatives, fats, lipoids, and mineral salts.

The isolated heparin concentrate is dried in a drier at 100° C. temperature to 90-95% dry substance content, and a fat-deficient concentrate is obtained with 0.2-1.6 mm grain size in the form of amorphous particles of large surface, storable for a long period, which is particularly suitable for extraction of heparin.

Advantages of the process according to the invention can be summed up as follows:

In the uniflow, single- or double-step extraction normally used for the production of heparin extracts, the programmed variation of the temperature, pH values and exploring chemicals is necessary. The counterflow extraction according to the invention is realizable in the same equipment by simple dissolution in an optimally selected aqueous alkaline medium, without changing the operative conditions or without the need for various chemicals.

The counterflow extraction results in the production of practically fat-free extracts of constant composition, of 5-10-times higher concentration than the usual extraction, in a short time and with satisfactory yield, than with the conventional methods.

Implementation of the counterflow extraction is not limited by chemical property of a given chemical, thus it takes place with the most suitable and inexpensive materials available.

The volumetric demand of the counterflow extraction in comparison with the conventional methods is reducible to $\frac{1}{4}$-1/10, the heparin-containing extract is available at uniform rate, concentrated in small volume, the volmetric capacity of the equipment is reducible, degree of utilization is improved.

For separating the heparin completely from the counterflow extraction system and for reducing the volume, delivery pumps and vacuum drum filters are sufficient, the continuous separation of the heparin is realizable with the feeding of quarternary ammonium compounds and protein solution of known composition and with the subsequent system acidification, with the isolation of the separating heparin-containing precipitate.

Reduction of the volume results in significant energy-saving, reduced labor force input, and in the use of less chemicals.

If the U-extractor described in the Hungarian patent No. 159 977 is used for implementation of the process according to the invention and the extraction is carried out with an extracting solution of 50° C. temperature, 0.5-1.0 n concentration, containing a minimum of 5% of sodium chloride in the extractor during a residence time of 30 minutes, then the active ingredient can be completely extracted from the heparin-containing organ concentrate. The ratio of the dried organ concentrate and extraction liquid is set to 1:5. The organ concentrate of large specific surface swells moderately with the intake of water, but it preserves its retentive granular character, and excellent filtering properties even at high alkaline concentration. Increase of the alkaline concentration practically hardly influences the amount of the dissolved non-heparin-like organic dry substance content, and the amount of dissolved proteins and peptides does not vary either.

EXAMPLE 1 (COMPARATIVE)

The heparin-containing raw material obtained as described above is extracted by a conventional method with autolysis in the presence of toluol and with the use of electrolyte solutions.

20 kg heparin raw material of the previous quality is intensively mixed with 100 kg fineground pig's small intestine of 18% dry substance content, 450 liter water and 150 liter 10% ammonium sulfate solution in a mixer duplicator. After mixing, the composite is heated to 38° C. After reaching 38° C. during constant mixing, 8.8–9.2 pH value is set with 40% sodium hydroxide, and in order to prevent harmful microbiological processes, 3 liter toluol is added into the system.

With the admission of enzymes the autolysis is continued for 36 hours, the temperature is kept at 38° C., and the system is periodically mixed. The pH value is checked at every 6 hours and in case of necessity the given pH value is maintained with 40% sodium hydroxide.

Following the 36 hour autolysis, the pH value is set between 7.3 and 7.7 with 18% hydrochloric acid and the composite is brought to boiling point. After boiling for 10 minutes the inert parts coagulate to the heat effect, these were separated on a sieve. The filtrate was separated from the fat at 60° C.

The obtained dark brown coloured extract liquid is 638 liter, heparin concentration 18.1 NE/ml, corresponding to 11.54 MNE heparin. The yield compared with example 5 is only 76%.

EXAMPLE 2 (COMPARATIVE)

The new type of heparin basic material of previous quality is extracted according to example 1 of the U.S. Pat. No. 3,817,831. 40 kg of the basic material is throroughly mixed with 400 liters of water in a mixer, the pH value is set to 2.7 with hydrochloric acid and the composite is heated to 38° C. Pepsin corresponding to 10 kg pig maw-mucosa is added and the pH value is set to the former value. The proteolysis is continued for 20 hours at constant mixing, the temperature is held at 37°–39° C.

After proteolysis for 20 hours, 8.0 pH value with 40 sodium hydroxide and 37° C. temperature are set, then 20 liters of activated pancreas mixture is added. The second proteolysis is kept on for 10 hours, the pH value checked every 2 hours and in case of necessity the given 8 pH value is maintained by adding sodium hydroxide. The temperature is set to 37° C. After the second proteolysis the composite is brought to boiling point, then filtered through sieve. The so-obtained brownish filtrate is 417 liters, heparin concentration 32.0 NE/ml, corresponding to 13.32 MNE heparin. Compared with example 5, the yield is 62.7%.

EXAMPLE 3 (COMPARATIVE)

The heparin raw material of quality specificed according to example 1, is processed with a process described in the Hungarian patent No. 148 776.

11.2 kg raw material is thoroughly mixed with 195 liter water in mixer duplicator, 6.5 kg sodium hydroxide is added, then the pH value is set to 10 with 40% sodium hydroxide. At uniform mixing, the temperature of the composite is increased with steam to 65° C., and treated with perioxide at this temperature. 250 ml 40% hydrogen peroxide is diluted with water to 4 liter, then 1 liter of the diluted mixture is mixed to the composite. The remaining 3 liters is added into the equipment at uniform rate during 30 minutes while the 65° C. temperature is maintained. After the peroxide treatment the composite is mixed at 65° C. for 1 hour, adding 600 g ammonium chloride, when the composite settles to 8.7 pH value. The composite is heated through the jacket of the duplicator until boiling point, after boiling for 5 minutes the heating and mixing are stopped. The composite is settled for 15 minutes, and the light yellow, completely transparent liquid over the extracted organ residue settled at the bottom of the equipment is decanted with the aid of the drain stub arranged on the side of the equipment. After decantation the mixture of the organ residue and water extract occupying about ¼ part of the equipment is poured after mixing onto a sieve with 0.8 mm mesh size.

Volume of the united extracts is 168 liters heparin concentration 32.4 NE/ml, corresponding to 5.44 MNE heparin yield. The yield compared with example 5 is only 72.4%.

EXAMPLE 4

5.0 kg haparin basic material of quality specified according to example 1, is divided into 10 equal parts and the 0.5 kg batches are processed according to the specifications of the intermittent counterflow extraction in 5 extraction steps. The extraction steps are carried out as follows:

The first batch of 0.5 kg dried organ is set to 3.2 liters extraction volume with 40° C. temperature, 6% sodium chloride containing 0.25 n sodium hydroxide solution. The composite is mixed at 40° C. temperature for 20 minutes. After 20 minutes the extract is filtered in vacuum with a Büchner funnel, the filter surface being a metal sieve with 0.6 mm mesh size. The first extraction filtrate is collected, its volume measured and the heparin activity is tested.

The wet organ retained on the sieve is mixed again with 40° C. temperature 6% sodium chloride containing 0.25 n sodium hydroxide solution and 3.2 liter extraction volume is set. The second extraction of the once already extracted organ is carried out as before. The second extraction filtrate of the first batch of the dried organ is mixed with the second 500 g dried organ batch and the extraction volume is set to 3.2 liters with the use of the former solutions.

The further steps are exactly the same as the sequence of the intermittent, 5-step counterflow extraction process. The extraction volume is always 3.2 liter, the temperature 40° C.

Volume and heparin activity of the collected extracts are the following:

| Serial Number | Volume of filtrate | Activity NE/ml | Heparin Content MNE |
|---|---|---|---|
| I. | 1770 | 83 | 0.147 |
| II. | 1810 | 118 | 0.214 |
| III. | 1790 | 133 | 0.238 |
| IV. | 1750 | 140 | 0.245 |
| V. | 1800 | 143 | 0.257 |
| VI. | 1770 | 153 | 0.271 |
| VII. | 1800 | 153 | 0.275 |
| VIII. | 1780 | 152 | 0.271 |
| IX. | 1815 | 149 | 0.270 |
| X/1. | 1790 | 153 | 0.274 |
| Step X./2 | 1800 | 52.5 | 0.095 |
| Step X./3 | 1850 | 16.4 | 0.030 |
| Step X./4 | 1830 | 5.2 | 0.009 |
| Step X./5 | 1780 | 1.8 | 0.003 |
| Total: | | | 2.599 |

According to the Table 2.599 MNE heparin is obtained from the 5.0 kg heparin-containing raw material of 90.4% dry substance content, with the use of the 5-step, intermittent, counterflow extraction. From the heparin activity of the extraction step of the 10th batch it is concluded that an exhaustive extraction took place. The yield is practically identical with that of example 5 (98.3%).

EXAMPLE 5

The heparin raw material of quality according to example 1 is extracted in counterflow system in U-extractor described in the Hungarian patent No. 159 977.

The dried basic material is continuously admitted into the extractor with screw feeder. Through the spray heads arranged above the feeder 0.55 n sodium hydroxide solution containing 6% sodium chloride of 70° C. temperature is added in a volume twice of the weight of the admitted product. Residence time of the material in the screw feeder is 10 minutes.

6% sodium chloride containing 0.1 n sodium hydroxide solution is added in counterflow with the swollen raw material admitted into the cells of the U-extractor. During the continuous counterflow extraction taking place in the equipment 50° C. temperature is maintained, and in order to facilitate the material transfer the material is subjected to shock motion with the vibrator arranged at the bottom of the U-extractor.

The continuously forming light yellow, nearly transparent extract liquid's volume is measured with a rotameter and the heparin concentration is determined with sample taken at every 30 minutes.

The heparin content of the continuously formed extract in the counterflow extraction system is separated likewise in continuous system, while the precipitation is obtained with drum filter for the purpose of further processing.

The processing is carried out in an equipment of 10 kg dried raw material capacity per hour, in which the residence time of the material is 35 minutes. After running for 10 hours the heparin activity is an average 252 NE/ml based on the sample taken from the 210 liters extract. This represents 52.9 MNE heparin yield related to the processed 100 kg product of 90.4% dry substance content.

Testing the wet organ residue discharged from the U-extractor for heparin activity, it was found that the counterflow extraction is realizable with a loss less than 2%.

The extracted organ residue can be marketed as excellent animal feed of high protein content.

What we claim is:

1. A process for the production of an aqueous extract with a heparin content of substantially 150 to 300 NE/ml, comprising the steps of:
    forming a heparin-enriched amorphous granular raw material containing 90 to 95% by weight dry substance from heparin-containing animal waste; and
    extracting said granular raw material by counterflow extraction at a temperature between 20° C. and 80° C. with an aqueous salt solution of an electrolyte composition of 1.5 to 12.0% and a pH of 8 to 12.8 or with an alkaline solution of 0.5 normal to 1.0 normal to form the aqueous extract.

2. The process defined in claim 1 wherein said counterflow extraction is carried out continously.

3. The process defined in claim 1 wherein said counterflow extraction is carried out intermittently.

4. The process defined in claim 1, claim 2 or claim 3 wherein the counterflow extraction is carried out in a vibrated U-extractor subdivided into cells.

* * * * *